United States Patent [19]

McKendry et al.

[11] Patent Number: 5,068,392

[45] Date of Patent: Nov. 26, 1991

[54] PROCESS FOR THE PREPARATION OF 2-CHLORO AND 2,6-DICHLOROANILINES

[75] Inventors: Lennon H. McKendry; Mark W. Zettler, both of Midland, Mich.

[73] Assignee: DowElanco, Indianapolis, Ind.

[21] Appl. No.: 645,176

[22] Filed: Jan. 24, 1991

[51] Int. Cl.$^5$ ............................................. C07C 229/00
[52] U.S. Cl. ..................................... 560/46; 558/414; 558/415; 558/416; 558/418; 560/47; 562/453; 562/456; 564/157; 564/167; 564/214; 564/218; 564/223; 564/412
[58] Field of Search ............... 558/414, 415, 416, 418; 560/46, 47; 562/453, 456; 564/157, 167, 214, 218, 223, 412

[56] References Cited

PUBLICATIONS

Brinelaw et al., *J. Chem. Soc.* 1208–1212 (1951).
Leeper et al., 5 *Proc. Int. Congr. Pest. Chem.*, 125–139 (1972).
*Organic Synthesis Collective* vol. 3, p. 262.
Short, *Chemical Abstracts*, vol. 60, No. 7938c (1964).
Bell, *Chemical Abstracts*, vol. 63, No. 13133e (1965).
Petyunin et al., *Chemical Abstracts*, vol. 52, No. 3763h (1958).
Hoshem et al., Chemical Abstracts, vol. 100, No. 6002g (1984).

*Primary Examiner*—Bruce Gray
*Attorney, Agent, or Firm*—Craig E. Mixan; Ronald G. Brookens

[57] ABSTRACT

2-Chloro and 2,6-dichloroanilines, optionally substituted in the 3-, 5-, and/or 6-position are prepared from the corresponding anilides by selective bromination, chlorination, reduction and hydrolysis. The selectivity of the process for introducing chlorines ortho to the amino group is very high.

11 Claims, No Drawings

PROCESS FOR THE PREPARATION OF 2-CHLORO AND 2,6-DICHLOROANILINES

FIELD OF THE INVENTION

The present invention concerns a process for preparing 2-chloro and 2.6-dichloroanilines, optionally substituted in the 3-, 5-. and/or 6-position, from the appropriate anilides already having substituents in the 3-, 5-, and/or 6-position. More particularly, the process of the present invention is characterized by the steps of a) bromination, b) chlorination and c)/d) reduction/hydrolysis.

BACKGROUND OF THE INVENTION

2-Chloro- and 2,6-dichloroanilines are useful as intermediates in the manufacture of a wide variety of chemical products including, for example, dyes, pharmaceuticals and agricultural chemicals. Unfortunately, 2-chloro and 2,6-dichloroanilines, optionally substituted in the 3-. 5-, and/or 6-position, are often not that easy to obtain. Because of the reactivity of the 4-position (para to the $NH_2$ group), this position must be blocked and subsequently deprotected to prevent overchlorination. For example, 2,6-dichloro-3-methylaniline is presently manufactured from the acetanilide of m-toluidine in a multistep process (see O. G. Backeberg et al., J. Chem. Soc., 1943, 78-80; and H. C. Brimelow et al., J. Chem. Soc., 1951, 1208-1212) involving the following reaction sequence:

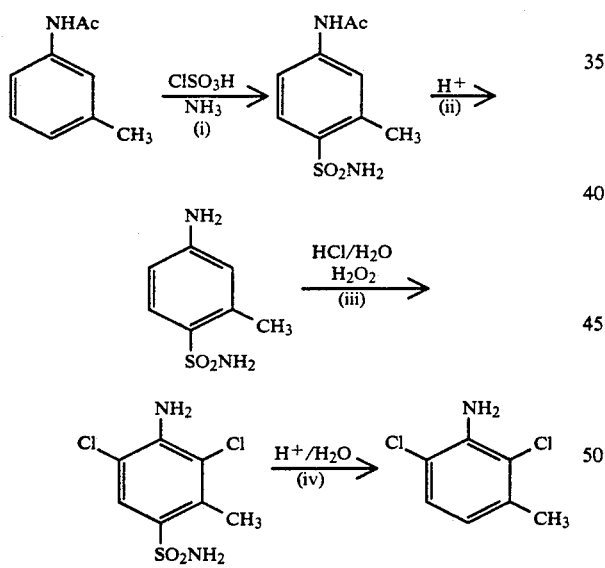

(i) protection of the p-position by sulfonamidation;
(ii) hydrolysis of the acetanilide;
(iii) chlorination of the 2- and 6-positions; and
(iv) deprotection of the p-position.

The yields of the protection (i) and chlorination (iii) steps are relatively low and the use of chlorosulfonic acid and ammonia present difficulties with respect to safe handling and waste disposal.

This it is desirable to have a process for safely and more economically producing 2-chloro and 2,6-dichloroanilines in good yield from readily available starting materials.

SUMMARY OF THE INVENTION

The present invention concerns a process for preparing 2-chloro and 2,6-dichloroanilines of the formula (I):

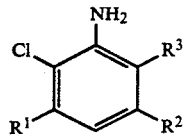

(I)

wherein
$R^1$ and $R^2$ are independently H, $C_1$-$C_4$ alkyl, $C_1$-$C_4$ alkoxy or Cl, and
$R^3$ is Cl, $CO_2R^4$, CN or $CONH_2$, where $R^4$ is H, $C_1$-$C_4$ alkyl or phenyl,
which comprises the following steps:
(a) brominating an anilide of the formula (II):

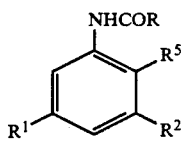

(II)

wherein
R is $CH_3$, $CH_2CH_3$ or $CF_3$,
$R^5$ is H, $CO_2R^4$, CN or $CONH_2$, and
$R^1$, $R^2$ and $R^4$ are as previously defined, to give a 4-bromoanilide of the formula (III):

(III)

wherein
R, $R^1$, $R^2$ and $R^5$ are as previously defined;
(b) chlorinating the 4-bromoanilide (III) of step (a) to give a 2-chloro or 2,6-dichloro-4-bromoanilide of the formula (IV):

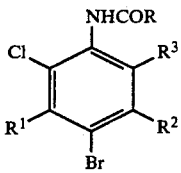

(IV)

wherein
R, $R^1$, $R^2$ and $R^3$ are as previously defined: and
(c) and (d) reducing and hydrolyzing the 2-chloro or 2.6-dichloro-4-bromoanilide (IV) of step (b) to give the 2-chloro or 2,6-dichloroaniline (I).

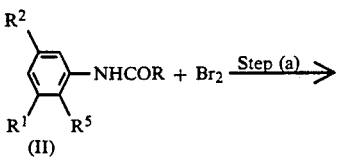

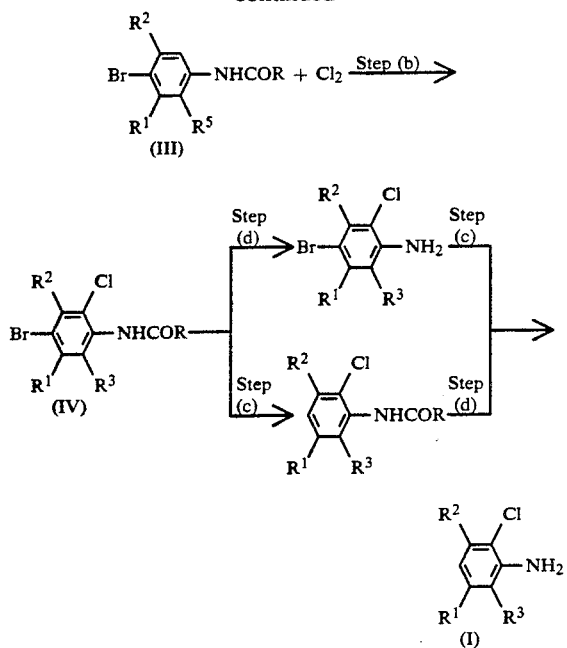

The reduction of the 4-bromo substituent (step c) and the hydrolysis of the anilide (step d) to give the free aniline can be conducted in any order.

By selectively brominating the 4-position, chlorines can effectively be directed selectively to the desired 2- and/or 6-positions. Selective reduction of the 4-bromo substituent and hydrolysis of the anilide provides the 2-chloro or 2,6-dichloroaniline in substantially higher yields than the prior art procedure.

Another aspect of the present invention is an improved process for the chlorination step in which the reaction is conducted in the presence of a bicarbonate/-water buffer.

A further aspect of the present invention is a process in which the 2-chloro or 2,6-dichloroaniline is prepared in an acetic acid based medium in a single reaction vessel.

DETAILED DESCRIPTION OF THE INVENTION

As used herein, the terms "C1-C4 alkyl" ano "$C_1$-$C_4$ alkoxy" refer to straight-chained or branched hydrocarbon groups of up to four carbon atoms, provided that all substituent groups are sterically compatiole with each other. The term "sterically compatible" is employed to designate substituent groups which are not affected by steric hindrance as this term is defined in "The Condensed Chemical Dictionary", 7th edition, Reinhold Publishing Co., N.Y. page 893 (1966) which definition is as follows: "steric hindrance: A characteristic of molecular structure in which the molecules have a spatial arrangement of their atoms such that a given reaction with another molecule is presented or retarded in rate."

Sterically compatible may be further defined as reacting compounds having substituents whose physical bulk does not require confinement within volumes insufficient for the exercise of their normal behavior as discussed in "Organic Chemistry" by D. J. Cram -nd G. Hammond, 2nd edition, McGraw-Hill book Company, N.Y., page 215 (1964).

The preferred "$C_1$-$C_4$ alkyl" and "$C_1$-$C_4$ alkoxy" groups are —CH3, —CH2CH3, —OCH3 and —OCH2CH3. The most preferred group is —CH3.

The 3-. 5-, and/or 6-substituted anilide (II) starting materials are known compounds and can be prepared from the corresponding anilines by conventional procedures, e.g.. with acyl halides or anhydrides of aoelic, propionic or trifluoroacetic acid. R is preferably —CH3; $R^1$ and $R^2$ are preferably independently hydrogen or —CH3; and $R^5$ is preferably H or $CO_2R^4$. In one of the more preferred embodiments, $R^5$ is hydrogen, and one of $R^1$ and $R^2$ is hydrogen and the other is —CH3. In another of the more preferred embodiments, $R^5$ is $CO_2R^4$, and $R^1$ and $R^2$ are hydrogen The selective bromination of the anilides (II) can be accomplished using a wide range of conventional brominating techniques and reagents. For the most part, regioselective bromination in the 4-position is favored by most procedures: conditions can generally be adjusted to limit undesirable over-bromination For example, the bromination can be accomplished with elemental bromine directly or with bromine chlorine (BrCl) which can be generated in situ, for example, from HBr and $Cl_2$. Other brominating agents like sodium bromate/HBr and N-bromosuccinimide work equally well. Optionally, the bromination can be conducted in the presence of typical electrophilic aromatic substitution catalysts, such as, for example, $FeCl_3$, in the presence of buffers, such as NaOAc, or in the presence of added HBr.

The bromination is performed in the presence of a solvent which is resistant or inert to the reaction conditions. A wide variety of solvents can be used ranging from water, to polar protic organic solvents like acetic acid, to relatively non-polar chlorinated hydrocarbons. The bromination process typically produces a slurry which can become quite intractable. For this reason, the initial concentration of anilide (II) is generally kept from about 5 to about 10 weight percent of the reaction mixture. Alternatively, higher initial proportions of reactant can be used if, for example, additional solvent or a compatible additive is introduced as needed to keep the slurry flowable. Because the reaction mixture is a multiphase system, efficient agitation is required.

In order to prevent over-bromination, the bromination is conducted at a temperature between the freezing point of the reaction mixture and 40° C., preferably between about 0° C. and ambient temperature.

In a typical bromination reaction, the starting anilide (II) and the solvent are mixed and cooled to below ambient temperature. The brominating agent is introduced at a rate commensurate with the rate of reaction and the rate of cooling. As the product precipitates, additional solvent or other compatible additive, eg. HBr, may be added to effect efficient agitation. The product can be isolated by conventional techniques or used as is in the subsequent chlorination.

If the anilide (11) is an acetanilide (R=$CH_3$), which is generally preferred, it is often most convenient to prepare the acetanilide directly from the corresponding aniline and acetic anhydride in acetic acid and to conduct the bromination in this acetic acid medium.

The chlorination of the 4-bromo anilides (III) to the 2-chloro or 2,6-dichloro-4-bromoanilides (IV) is readily accomplished by contacting the 4-bromoanilide with chlorine in the presence of an appropriate solvent. By controlling reaction conditions, the desired mono- or dichlorination can be made to predominate. Similarly, conditions should be controlled to minimize the substitution of chlorine for bromine in the 4-position.

The contacting of the ingredients is performed in the presence of a polar protic organic solvent, such as, for example, alkanoic acids like acetic acid or trifluoroacetic acid, or a polar aprotic organic solvent, such as, for example, alkylnitriles like acetonitrile. The solvent must be resistent or inert to chlorination. It is usually preferable to conduct the reaction in mixtures of the polar organic solvents with water. In general, ratios of polar organic solvent to water of from 3:1 to 100:1 on a weight basis are employed. Ratios of polar organic solvent to water of from 4 1 to 50:1 are preferred. The solvent is employed in an amount sufficient to at least slurry the ingredients and to keep the mixture tractable throughout the reaction. Typically, the concentration of the 4-bromoanilide is from about 5 to about 30 weight percent of the mixture with the solvent media.

In the absence of added water, it may be desirable to conduct the chlorination in the presence of a metal halide catalyst. By metal halide catalyst is meant any of the Lewis acid catalysts typically employed in electrophilic aromatic halogenation reactions. The metal halide catalysts include but are not limited to compounds of the formula $$M^n X_n$$

wherein

M is aluminum (Al), boron (B), iron (Fe), antimony (Sb), tin (Sn) or titanium (Ti):

X is chloro, bromo or fluoro: and n is an integer which is the oxidation state of the metal.

Preferably, M is aluminum, iron or antimony and X is chloro. For aluminum, iron and antimony, n is preferably 3. Catalysts which can conveniently be employed include: aluminum chloride, aluminum bromide, boron trifluoride, ferric chloride, titanium chloride, antimony chloride and the like. Aluminum chloride and ferric chloride are usually preferred.

The metal halide catalyst is used in amounts of from about 0.1 to about 20 weight percent of the 4-bromo anilide initially charged. Catalyst levels in the range of from 1.0 to 10 weight percent are generally preferred. The metal halide catalyst should be maintained anhydrous or as water-free as possible, since water can chemically react and deactivate the catalyst.

To avoid overchlorination, i.e., substitution of chlorine for bromine in the 4-position, the reaction is generally run at a temperature between the freezing point of the mixture and about 40° C. The preferred temperature range is from about 0° C. to ambient. Although superatmospheric pressures can be employed, operation at atmospheric pressure is often more convenient.

Chlorine can be slowly introduced by bubbling into the reaction mixture. Preferably, the chlorine should be added at a rate commensurate with the reaction rate and the rate of cooling. Ideally, an amount from about 1.0 to about 2.5 equivalents of chlorine per equivalent of 4-bromoanilide are employed. Normally from about 1.G to about 1.1 equivalents for each position to be chlorinated are preferred. Larger excesses of chlorine can be used, but they generally lead to increased amounts of overchlorination.

Since HCl is produced in the chlorination reaction, a buffer may be optionally employed.

With a 4-bromoanilide for example, during the course of a typical chlorination reaction using a stoichiometric amount of chlorine, the reaction was found to slow dramatically once a ratio of monochlorinated to dichlorinated material of 25:75 was reached.

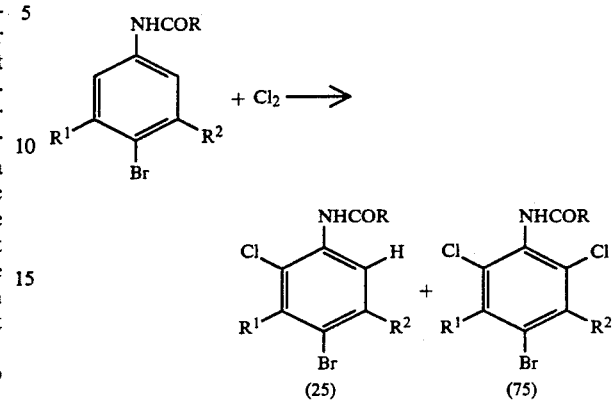

Complete chlorination required 6-16 hr (hr), of which 3-13 hr was required to convert the final 25 percent monochlorinated material to product. Although the rate could be accelerated by using excess chlorine, this generally increases the amount of overchlorination. Although buffers in general, such as NaOAc, Na$_2$SO$_4$, NH$_4$OAc, Na$_2$HPO$_4$ and NaH$_2$PO$_4$ help maintain the pH of the reaction mixture and allow the reaction to go to completion, they do not greatly accelerate the rate of reaction. It has been found that bicarbonate, when added in less than stoichiometric amounts with respect to the HCl generated, i.e., from about 0.5 to about 2.0 equivalents, unexpectedly accelerates the rate of reaction significantly. By bicarbonate is meant an alkali metal bicarbonate such as LiHC0$_3$, NaHC0$_3$ or KHCO$_3$.

This discovery represents another aspect of the present invention, viz., a process for the preparation of a 2,6-dichloro-4-bromoanilide of formula (IV)

![structure IV]

(IV)

wherein:

R is CH$_3$, CH$_2$CH$_3$ or CF$_3$, and

R$^1$ and R$^2$ are independently H, C$_1$-C$_4$ alkyl, C$_1$-C$_4$ alkoxy or Cl, consisting essentially of contacting a 4-bromoanilide of formula (III)

![structure III]

(III)

wherein

R, R$^1$ and R$^2$ are as previously defined, with from 1.8 to 2.5 equivalents of chlorine in a solvent consisting of from 3:1 to 100:1 parts of an alkanoic acid per part of water in the presence of from 0.5 to 2.0 equivalents of alkali metal bicarbonate at a temperature between about 40° C. and the freezing point of the mixture.

In a typical reaction according to this aspect of the invention, the starting material, alkanoic acid, water and bicarbonate are mixed at the appropriate temperature and chlorine is gradually introduced. Upon completion of the reaction, the product can be isolated by conventional procedures or the reaction mixture can be used in the next step of the sequence.

The reduction and hydrolysis of 2-chloro or 2,6-dichloro-4-bromoanilides (IV) to 2-chloro or 2,6-dichloroanilines (1) can be conducted in any order.

In the reduction step, either a 2-chloro or 2,6-dichloro-4-bromoanilide or a 2-chloro or 2,6-dichloro-4-bromoaniline is reacted with hydrogen in the presence of a supported noble metal catalyst During the course of the reaction, the bromine in the 4-position is selectively replaced by hydrogen. By a supported noble metal catalyst is meant any noble metal catalyst on a variety of supports that selectively effects the reduction of the bromo substituent. Such catalysts include but are not limited to platinum, palladium and ruthenium. Typical supports include silica, alumina, magnesia and carbon. The preferred catalysts are platinum and palladium supported, for example, on carbon. The most preferred catalysts range from 0.5 to 10 percent palladium on carbon. Generally, 0.001 to 0.05 equivalents of noble metal are employed per equivalent of substrate; from 0.01 to 0.03 equivalents are preferred.

The reduction is conveniently conducted with an excess of hydrogen. For example, hydrogen gas can be continuously sparged into the reaction mixture at atmospheric pressure. Alternatively, a sealed reactor can be pressurized with hydrogen gas.

The reduction is generally performed in an organic solvent that is inert to the reaction conditions. Alcohols and carboxylic acids and their esters are particularly preferred. In this context, the term alcohol refers to straight-chained or branched aliphatic alcohols of from 1 to 6 carbon atoms. The term carboxylic acid refers to straight-chained or branched alkanoic acids of from 1 to 4 carbon atoms. Appropriate esters are those prepared from the acids and alcohols indicated above. Examples of the preferred solvents include methanol, ethanol, propanol, acetic acid, propionic acid and ethyl acetate. The alcohols and carboxylic acids can be used in admixture with water in ratios of organic solvent to water of from 3:1 to 100:1.

The reduction is generally carried out at a temperature from about 0° to about 65° C., preferably from ambient to about 50° C. Higher temperatures can result in over-reduction. Operating pressures, although not critical, may also affect the amount of reduction. The pressure may typically vary from atmospheric pressure to about 700 pounds per square inch gauge (psig). Pressures from atmospheric to about 200 psig are preferred.

Since the reduction of the aromatic bromine produces hydrogen bromide, it is often advantageous to add an HBr acceptor to buffer the system. At least one equivalent of base should be added for each equivalent of HBr produced.

In a typical reduction reaction, for example, a 2,6-dichloro-4-bromoanilide is suspended in acetic acid/water under nitrogen at room temperature. One equivalent of NaOH is added to scavenge the HBr generated and the mixture is stirred at from ambient temperature to about 65° C. From about 0.1-5 mole percent of 5-10 percent palladium on carbon is added and the system is repurged with nitrogen. Hydrogen is then bubbled into the reaction until one equivalent has been consumed. After removal of the catalyst, the product can be isolated by conventional techniques.

Hydrolysis of the 2-chloro or 2,6-dichloro-4-bromoanilide or the 2-chloro or 2,6-dichloroanilide to the corresponding aniline is conveniently achieved by contacting the anilide with water under either basic or acidic conditions. Such hydrolyses are well-known to those skilled in the art and are generally conducted in organic solvents that are miscible with water. For example, the anilide can be hydrolyzed to the aniline by refluxing in a mixture of alcohol and water in the presence of a base like NaOH. Similarly, hydrolysis of the anilide can be effected by reflux in a mixture of either an alcohol or a carboxylic acid and water in the presence of an acid like HCl. The resulting aniline can be isolated by routine laboratory techniques.

Ideally it would be desirable to conduct the entire series of reactions, i. e., the bromination, chlorination, reduction and hydrolysis, in a single reaction medium and to avoid the isolation of intermediate products. Another aspect of the present invention concerns such an integrated process, viz., one in which the steps are consecutively performed in an acetic acid medium without isolation of intermediates. Furthermore, with an acetic acid based solvent system, the overall process can be extended to include the starting acetanilides in which R is CH3 Thus, the present invention also concerns a process for preparing 2-chloro or 2,6-dichloroanilines of the formula (I):

wherein
R$^1$ and R$^2$ are independently H, C$_1$-C$_4$ alkyl, C$_1$-C$_4$ alkoxy or Cl, and
R$^3$ is Cl, CO$_2$R$^4$, CN or CONH$_2$, where
R$^4$ is H, C$_1$-C$_4$ alkyl or phenyl,
which comprises conducting the following steps in an acetic acid based medium without isolation of the intermediates:

(a) acetylating an aniline of formula (V):

wherein
R$^5$ is H, CO$_2$R$^4$, CN or CONH$_2$, and
R$^1$, R$^2$ and R$^4$ are as previously defined, to give an anilide of formula (IIa):

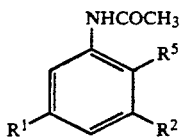

(IIa)

wherein
R¹, R² and R⁵ are as previously defined:
(b) brominating the anilide (IIa) of step (a) to give a 4-bromoanilide of formula (IIIa):

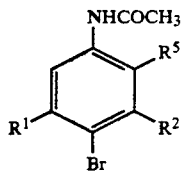

(IIIa)

wherein
R¹, R² and R⁵ are as previously defined;
(c) chlorinating the 4-bromoanilide (IIIa) of step (b) to give a 2-chloro or 2,6-dichloro-4-bromoanilide of the formula (IVa):

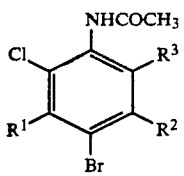

(IVa)

wherein
R¹, R² and R³ are as previously defined: and
(d) and (e) reducing and hydrolyzing the 2-chloro or 2,6-dichloro-4-bromoanilide (IVa) of step (c) to give the 2-chloro or 2,6-dichloroaniline (I).

In the acetylation reaction, aniline (V) is contacted with acetic anhydride in acetic acid solvent. In general, a slight stoichiometric excess (1-10 mole percent) of acetic anhydride is employed to ensure complete acetylation. Incomplete acetylation results in over halogenation or oxidation of residual aniline in the subsequent bromination and chlorination steps.

Bromination in the integrated process is preferably accomplished using bromine chloride (BrCl). Typically, 0.5 equivalents of bromine are introduced with stirring into the reaction mixture containing acetanilide (IIa) in acetic acid. The temperature is maintained below 20° C. to prevent over bromination. After the bromination of one half of the acetanilide is complete, 0.5 equivalents of chlorine are introduced. The Cl2 reacts with HBr to generate BrCl which completes the bromination process.

Once bromination is complete, 1.0 to 1.25 equivalents of bicarbonate per equivalent of chlorine, dissolved in warm (50°-70° C.) water, are slowly added to the reaction mixture. The resulting solution is then chlorinated by contacting with from 0.95 to 1.0 equivalents of chlorine per position to be chlorinated at a temperature below 30° C.

Residual chlorine has a deleterious effect on catalytic hydrogenolysis. Therefore, catalyst lifetime can be improved by limiting the amount of chlorine introduced in the chlorination step to less than stoichiometric amounts. Alternatively, the chlorination solution may be passed through a carbon bed to remove potential catalyst poisons.

After chlorination is complete, 1 or 2 equivalents of NaOH or KOH are added to the reaction mixture which is either diluted with additional HOAc or heated until a homogeneous solution is obtained. The system is purged with nitrogen after which 1 to 5 mole percent of catalyst (5 to 10 percent Pd on carbon) is added. The mixture is contacted with hydrogen and, after the completion of the reduction, the catalyst is removed by filtration.

To facilitate subsequent isolation, about 50 percent of the acetic acid can be removed by distillation after filtration of the catalyst. Hydrolysis is conveniently accomplished by the addition of aqueous HCl followed by reflux. The product can be isolated by azeotropic distillation from the reaction mixture and can be purified by conventional laboratory techniques such as fractional distillation or crystal refining.

The following examples are presented to illustrate the invention and should not be construed as limiting the scope of the invention. All melting points are uncorrected.

EXAMPLE A

Preparation of N-(3-Methylphenyl)acetamide Starting Material

To a stirred solution of 11.2 grams (g) (0.11 mole) of acetic anhydride in 100 milliliters (mL) of acetic acid, was added 10.7 g (0.1 mole) of m-toluidine. The solution exothermed to 35° C. and, ten minutes (min) after all the m-toluidine was added, the product solution was concentrated in vacuo. The residue was taken up in EtOAc and was washed with $H_2O$. The organic layer was dried over $MgSO_4$ and concentrated in vacuo to give 14.46 g (97%) of product as a white powder (m.p. 65°-66° C). $^1H$ NMR (CDCl₃) δ:9.2 (1H, s, NH), 7.2 (2H, d, 8 Hz, aromatic), 7.0 (1H, t, 8 Hz, aromatic), 6.7 (1H, d, 8.0 Hz, aromatic).

EXAMPLE 1

Preparation of N-(4-Bromo-3-methylphenyl)-acetamide m-Toluidine (1.0 mole, 107 mL) was added dropwise to a solution of acetic anhydride (1.05 mole, 107.2 g, 99 mL) in acetic acid (500 mL) with cooling (maintain temp. ≦25° C.). After stirring 30 min, bromine (159.8 g) was added dropwise, over 60 min with continued cooling. After one half of the bromine was added, HBr (25 mL of 48% HBr) was added in one portion. A second 25 mL portion of HBr was added after 3/4 of the bromine had been added. A final 25 mL portion of HBr was added after the addition of Br₂ was completed. The mixture was stirred for 30 min after which the mixture was concentrated in vacuo and was taken up in $H_2O$ and EtOAc. The layers were separated and the organic layer was washed with $H_2O$ and 10% $Na_2CO_3$ solution, dried over $MgSO_4$ and concentrated to afford 216 g (95%) of product as a creamy white solid (m.p. 101°-102° C). $^1H$-NMR (CDCl₃) δ 8.2 (1H, br s, NH), 7.4 (2H, dd, 3.0 Hz, 8.0 Hz), 7.2 (1H, dd, 8.0 Hz, 3.0 Hz), 2.2 (3H, s, Ph-CH₃), b 2.08 (3H, s, COCH₃). $^{13}C$(CDCl₃) δ 168, 138, 137, 132, 122, 119, 24, 23 ppm.

EXAMPLE 2

Preparation of N-(4-Bromo-3methylphenyl)-acetamide

A series of bromination reactions of N-(3-methylphenyl)acetamide were conducted with a variety of brominating agents at or below ambient temperature. The procedure was similar to Example 1. The product was analyzed by gas chromatography. The results are summarized in Table I.

TABLE I
BROMINATION of N-(3-METHYLPHENYL)ACETAMIDE

| REAGENTS | PRODUCT (%) | | |
|---|---|---|---|
| | 1 | 2 | 3 |
| Br$_2$/AcOH | 96.8 | TR[2] | 2.5 |
| Br$_2$/AcOH/NaOAc | 97.8 | TR | 2.1 |
| Br$_2$/HBr/AcOH | 98.5 | 0.3 | 0 |
| Br$_2$/HCl/H$_2$O | 88.0 | 1.4 | 10.7 |
| NaBrO$_3$/HBr | 96.0 | 0.4 | 0 |
| (NaBrO$_3$/H$_2$O)/HBr | 98.2 | 0.72 | 0 |
| NBS/DMF[1] | 80.7 | TR | 0 |
| Br$_2$/H$_2$O | 90 | 0.9 | 9 |
| ½Br$_2$/½Cl$_2$ | 95 | TR | 1.5 |

[1]N-Bromosuccinimide in dimethylformamide
[2]TR is "trace"

EXAMPLE 3

Preparation of N-(2,6-Dichloro-4-bromo-3-methylphenyl)acetamide

N-(4-Bromo-3-methylphenyl)acetamide (0.1 mole, 22.8 g) was slurried into acetic acid (225 mL) and H$_2$O (25 mL). Chlorine (2.0 mole, 14.2 g) was bubbled into the reaction mixture at room temperature over 60 min and the mixture was stirred 5-16 hrs. The product mixture was poured into aqueous HCl (6.25 N, 200 mL) and filtered. The filter cake was washed with H$_2$O and dried in vacuo at 60° C. to give 22.9 g (87.4%) of product as an off-white solid (m.p. 173°-174° C.). 1H NMR (DMSO) δ 9.9 1H, s, Ph—NH—Ac), 7.63 (1H, s), 2.45 (3H, s, Ph—CH$_3$), 2.06 (3H, s, NHCOCH$_3$). $^{13}$C NMR (DMSO) δ168.5, 135.3, 34.7, 133.1, 131.6, 130.8, 122.8, 22.4, 20.9 ppm.

EXAMPLE 4

Preparation of N-(2,-Dichloro-4-bromo-3-methylphenyl)acetamide

A series of chlorination reactions was conducted with a variety of solvent systems and buffers. In general, from 0.5 to 1.5 equivalents of buffer were added prior to addition of chlorine. Procedures were similar to Example 3. The product was analyzed by gas chromatography and the results are summarized in Table II.

TABLE II
CHLORINATION OF N-(4-BROMO-3-METHYLPHENYL)-ACETAMIDE

| Run | SOLVENT (ratio) | BUFFER | TIME (hrs) | PRODUCT (%) | | |
|---|---|---|---|---|---|---|
| | | | | 1 | 2 | 3 |
| 1 | AcOH[1]/H$_2$O (9:1) | — | 16 | 92 | 1.2 | 6.8 |
| 2 | ACN[2]/H$_2$O (20:1) | — | 16 | 87 | 1 | 6.5 |
| 3 | ACN/H$_2$O (20:1) | Na$_2$SO$_4$ | 16 | 89.6 | 1.7 | 7.4 |
| 4 | AcOH/H$_2$O (10:1) | NaOAc | 16 | 89 | 3 | 6 |
| 5 | ACN/H$_2$O (4:1) | NaOAc | 16 | 88 | 7 | 3 |
| 6 | AcOH/H$_2$O (4:1) | NaHCO$_3$ | 3 | 86 | 0 | 8 |
| 7 | AcOH/H$_2$O (4:1) | Na$_2$HPO$_4$ | 16 | 74 | 5 | 6 |
| 8 | AcOH/H$_2$O (4:1) | KHCO$_3$ | 3 | 82 | 2 | 8 |
| 9 | AcOH/H$_2$O (80:20) | NaH$_2$PO$_4$ | 16 | 81 | 7 | 5 |
| 10 | AcOH/H$_2$O (9:1) | NH$_4$OAc | 16 | 94 | 2 | 4 |

[1]acetic acid
[2]acetonitrile

EXAMPLE 5

Preparation of N-(2,6-Dichloro-3-methylphenyl)acetamide

N-(2,6-Dichloro-4-bromo-3-methylphenyl) e (30.88 g) was dissolved into AcOH (500-725 mL) at room temperature under a nitrogen atmosphere. NaOH (8.0 g, 50 percent aqueous) was added followed by Pd/C (11.1 g of 5 percent Pd on carbon). Hydrogen (2330 mL) was bubbled into the vapor space over 75 min after which the catalyst was filtered away from the product solution The product mixture was concentrated, taken up in EtOAc/H$_2$O, separated, washed with H$_2$O and 10% NaHCO$_3$, dried over MgSO$_4$ and concentrated to give 22.44 g of white powder. After recrystallization from ethyl acetate, the product had a m.p. 180.5°-181.5° C.

EXAMPLE 7

Preparation of 2,6-Dichloro-3-methylaniline

N-(2,6-Dichloro-3-methylphenyl)acetamide (22 g) was suspended in HCl (5.0 N, 100 mL), H$_2$O (300 mL) and propanol (or AcOH, 20-50 mL). The mixture was refluxed for several hr after which the solution was cooled, chloride (3×200 mL). The organic extractions were combined, washed with water, dried over MgSP$_4$, and concentrated to give 16 g of product as a low melting solid (m.p. 36°–38° C.). $^1$H NMR (CCl$_4$) δ6.97 (d, 9.0), 6.46 (d, 9.0 Hz, 1H), 2.28 (s, 3H, CH$_3$)

EXAMPLE 7

Preparation of 2,6-Dichloro-4-bromo-3-methylaniline

A solution consisting of 2.07 g of N-(2,6-dichloro-4-bromo-3-methylphenyl)acetamide, 50 mL of ethanol, 25 mL of water and 25 mL of 50 percent NaOH were refluxed until hydrolysis was complete. The reaction mixture was cooled and extracted with ethyl ether. The extract was washed with water, dried over MgS04 and filtered. Removal of the solvent under reduced pressure gave 1.6 g of white solid. The product was purified by elution with pentane from a silica gel column and recrystallization from heptane (m.p. 67–69° C). $^1$H NMR (CCl$_4$) δ7.33 (s, 1H), 4.40 (s, 2H, NH$_2$), 2 40 (s, 3H, CH$_3$).

EXAMPLE 8

Preparation of 2,6-Dichloro-3-methylaniline ( A 100-ml flask containing a side arm sealed with a serum cap was equipped with a stir bar, purged with N2, and 1.16 g of 2,6-dichloro-4-bromo-3-methylaniline, 15 mL of EtOAc, 375.7 mg of NaOAc, and 71.3 milligrams (mg) of 5 percent Pd/C added. The flask was equipped with a 3-way stopcock to which was connected a balloon filled with H2 to an 18 cm diameter. The flask was cooled in an ice bath and evacuated and filled with H$_2$ three times. The mixture was stirred at room temperature for 6.5 hr. The H$_2$ source was removed and the flask evacuated and filled with air. The reaction mixture was filtered through Celite, and the flask and filter rinsed with EtOAc. The solvent was removed in vacuo. The residue was purified by elution with pentane from a silica column. Evaporation of the eluent provided 0.87 g of white solid (m.p. 35°–36° C.).

EXAMPLE 9

Preparation of 2,6-Dichloro-3-methylaniline from 3-Methylaniline in an Acetic Acid Medium 3-Methylaniline (1.0 mol, 107.16 g) was added dropwise to a solution of Ac$_2$O (110 mL) in AcOH (2200 mL) in a 4 liter, glass-lined, reactor equipped with an air-driven, over-head stirrer, dropping funnel, dry ice condenser and a gas inlet tube. Cooling was provided by circulating a constant temperature ethylene glycol/-water mixture through the jacketed reactor (20° C.). Once acylation was complete, bromine (0.5 mol, 79.91 g) was added dropwise over 30 minutes at 20° C. The reaction was stirred an additional 30 minutes, during which time a white precipitate formed. Chlorine (0.5 mol, 35.45 g) was then bubbled into the reactor at 20° C. over 40 minutes. Chlorine filled the vapor space of the reactor during the addition, however, after stirring an additional 30 minutes, chlorine vapors were no longer noticeable Cooling was discontinued and aqueous KHCO$_3$ (250 g/500 mL) was added over several minutes, during which time the white slurry turned into a homogeneous, water clear solution. The addition of bicarbonate was accompanied by a 6° C. exotherm (20°–26° C.). After stirring several minutes, chlorine (141.8 g) was again added to the reaction After 2.5 g of chlorine were added, the solution turned dark yellow. After 14 g of chlorine were added, the solution was once again water clear. All the chlorine was added over two hr after which the yellow solution stirred an additional hr. The reaction was kept at 30° C. during the chlorination process. Once chlorination was complete, sodium hydroxide (80 g of a 50 percent aqueous solution) was added and the reaction was heated, under nitrogen, until all organic material was dissolved (65°–70° C.). Palladium (21.2 g of 10 percent Pd on carbon, 2 mole percent) was added after which hydrogen was bubbled into the reactor. Once hydrogenolysis was complete, the solution was filtered and 1100 mL of acetic acid were distilled from the product solution. H$_2$O (1000 mL) and HCl (500 mL of 6.25 N HCl) were added to the resulting solution and the whole was refluxed for several hr to complete hydrolysis. 2,6-Dichloro-3-methylaniline was then collected in a Dean Stark trap by azeotropic distillation (125.97 g, 71.6%) over 32 hr.

EXAMPLE 10

Preparation of N-(2-Carbomethoxyphenyl)-acetamide

A solution consisting of 20 mL of acetic anhydride in 100 mL of methylene chloride was stirred at room temperature and 20 mL of methyl anthranilate (0.113 mole) was added dropwise over 10 min. Triethylamine (20 mL, 0.14 mole) was added and the solution was stirred at room temperature for 18 hr. An additional 100 mL of methylene chloride was added followed by 20 mL of water while cooling in an ice bath. The phases were mixed and the organic layer was separated. The aqueous layer was extracted with 20 mL of methylene chloride and the combined organic layers were dried over anhydrous sodium sulfate. Evaporation of the solvent afforded 20.05 g of product as a white solid (m.p. 96°–97° C.). $^1$H NMR (CDCl$_3$) δ8.66 (d, 8.0 Hz, 1H), 8.02 (dd, 8.0 Hz, 2.0 Hz, 1H), 7.53 (dt, 8.0 Hz, 2.0 Hz, 1H), 7.03 (t, 8.0 Hz, 1H), 3.98 (s, 3H, OCH$_3$), 2.27 (s, 3H, COCH$_3$).

EXAMPLE 11

Preparation of N-(2-Carbomethoxy-4-bromo-phenyl)acetamide

A stirred solution consisting of 14.8 g of N---(2-carbomethoxyphenyl)acetamide and 75 mL of acetic acid was cooled in an ice-acetone bath and 6 mL of bromine were added dropwise. The cooling bath was removed and the solution was stirred for 17 hr. The solution was diluted with 100 mL of methylene chloride and was washed with water. The organic phase was dried over anhydrous sodium sulfate and the solvent was removed in vacuo. The product was purified by elution from a silica gel column with 9:1 methylene chloride: ethyl acetate, which afforded 17.9 g of product as a white solid (m.p. 131°–133° C.). $^1$H NMR (CDCl$_3$) 88.66 (d, 9.0 Hz, 1H), 8.15 (d, 2.0 Hz, 1H), 7.63 (dd, 9.0 Hz, 2.0 Hz, 1H), 3.98 (s, 3H, OCH$_3$), 2.27 (s, 3H, COCH$_3$).

EXAMPLE 12

Preparation of N-(2-Carbomethoxy-4-bromo-6-chlorophenyl)acetamide

A solution containing 10 g of N-(2-carbomethoxy-4-bromophenyl)acetamide (0.0368 mole) in 200 mL of trifluoroacetic acid was stirred and 7.2 g of sodium acetate was added The flask was purged with nitrogen and the contents were then stirred under a chlorine atmosphere (excess) at ambient temperature for 16 hr. The trifluoroacetic acid was removed in vacuo, and the residue was treated with 100 mL of water and 1 g of sodium bisulfite. The mixture was stirred for 1.5 hr and then was extracted with ethyl acetate. The organic layer was dried over anhydrous sodium sulfate and the solvent was removed in vacuo. The product was purified by elution from a silica gel column with 200 mL of 1:9 ethyl acetate : hexane followed by 1:1 ethyl acetate: methylene chloride. Product was isolated as a white solid, 9.9 g (m.p. 152°–153° C.). $^1$H NMR (CDCl$_3$) $\delta$7.97 (d, 2.0 Hz, 1H), 7.75 (d, 2.0 Hz, 1H), 3.98 (s, 3H, OCH$_3$), 2.27 (s, 3H, COCH$_3$).

EXAMPLE 13

Preparation of N-(2-Carbomethoxy-6-chlorophenyl)acetamide

In a hydrogenation apparatus was placed 3.1 g of N-(2-carbomethoxy-4-bromo-6-chlorophenyl)acetamide and 100 mL of ethanol. The apparatus was purged with nitrogen and 0.1 g of 10 percent palladium on charcoal was added. The mixture was agitated under a hydrogen atmosphere at 40 psig for 2 hr at ambient temperature. The mixture was filtered to remove the catalyst, and the solvent was removed from the filtrate under reduced pressure. The product was purified by elution from a silica gel column using a gradient of 9:1 to 1:1 methylene chloride : ethyl acetate as the eluent to give 1.8 g of white solid (m.p. 135°–136° C.). $^1$H NMR (acetoned$_6$+CDCl$_3$) $\delta$7.92 (d with fine coupling, 8.0 Hz, 1H), 7.74 (d with fine coupling, 8.0 Hz, 1H), 7.46 (t, 8.0 HZ, 1H), 3.98 (s, 3H, OCH$_3$), 2.55 (s, 3H, COCH$_3$).

EXAMPLE 14

Preparation of 2-Carbomethoxy-6-chloroaniline (Methyl 3-Chloroanthranilate)

A stirred solution of 0.1 g (2.3 mmole) of N-(2-carbomethoxy-6-chlorophenyl)acetamide in 10 mL of methanol containing 0.2 mL of conc. H2S04 was heated at reflux for ca. 18 hr. The methanol was removed in vacuo and the residue treated with 5 mL of EtOAc and 5 mL of H$_2$O respectively. The phases were mixed and separated. The aqueous layer was extracted with 2×5 mL of EtOAc and the combined EtOAc solution dried (Na$_2$SO$_4$), filtered, and the solvent removed from the filtrate in vacuo. The product was purified by preparative thin layer chromatography (TLC) using 9:1 (v/v) CH$_2$Cl$_2$ EtOAc. The band containing product was extracted with EtOAc and filtered. The solvent was removed from the filtrate in vacuo to afford 78 mg (91% yield) of methyl 3-chloroanthranilate as a light yellow solid: $^1$H NMR (CDCl$_3$, TMS) $\delta$7.80 (d, 8 Hz, H$_6$), 7.39 (d, 8 Hz, H$_4$), 6.55 (t, 8 Hz, H$_5$), 6.25 (broad s, NH$_2$), 3.90 (s, OCH$_3$).

What is claimed is:

1. A process for preparing 2-chloro and 2,6-dichloroanilines of the formula (I):

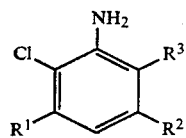

wherein $R^1$ and $R^2$ are independently H, C$_1$–C$_4$ alkyl, C$_1$–C$_4$ alkoxy or Cl, and $R^3$ is Cl, CO$_2$R$^4$, CN or CONH$_2$, where $R^4$ is H, C$_1$–C$_4$ alkyl or phenyl, which comprises the following steps:

(a) brominating an anilide of the formula (II):

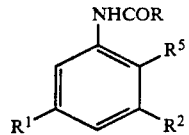

wherein

R is CH$_3$, CH$_2$CH$_3$ or CF$_3$, $R^5$ is H, CO$_2$R$^4$, CN or CONH$_2$, and $R^1$, $R^2$ and $R^4$ are as previously defined, to give a 4-bromoanilide of the formula (III):

wherein

R, $R^1$, $R^2$ and $R^5$ are as previously defined:

(b) chlorinating the 4-bromoanilide (III) of step (a) to give a 2-chloro or 2,6-dichloro-4-bromoanilide of the formula (IV):

wherein

R, $R^1$, $R^2$ and $R^3$ are as previously defined; and (c) and (d) reducing and hydrolyzing the 2-chloro or 2,6-dichloro-4-bromoanilide (IV) of step (b) to give the 2-chloro or 2,6-dichloroaniline (I).

2. The process of claim 1 in which R is —CH$_3$.

3. The process of claim 1 in which $R^1$ and $R^2$ are independently hydrogen or —CH$_3$.

4. The process of claim 1 in which $R^5$ is hydrogen or CO$_2$R$^4$.

5. A process for preparing 2-chloro or 2,6-dichloroanilines of the formula (I):

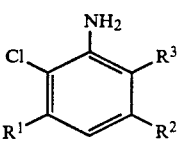

wherein $R^1$ and $R^2$ are independently H, C$_1$–C$_4$ alkyl, C$_1$–C$_4$ alkoxy or Cl, and $R^3$ is Cl, CO$_2$R$^4$, CN or CONH$_2$, where $R^4$ is H, C$_1$–C$_4$ alkyl or phenyl, which comprises conducting the following steps in an acetic acid based medium without isolation of the intermediates:

(a) acetylating an aniline of formula (V):

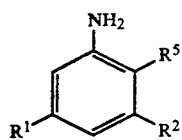

wherein $R^5$ is H, $CO_2R^4$, CN or $CONH_2$, and $R^1$, $R^2$ and $R^4$ are as previously defined, to give an anilide of formula (IIa):

wherein $R^1$, $R^2$ and $R^5$ are as previously defined;

(b) brominating the anilide (IIa) of step (a) to give a 4-bromoanilide of formula (IIIa):

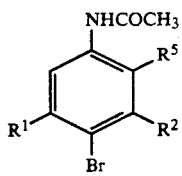

wherein $R^1$, $R^2$ and $R^5$ are as previously defined:

(c) chlorinating the 4-bromoanilide (IIIa) of step (b) to give a 2-chloro or 2,6-dichloro-4-bromoanilide of the formula (IVa):

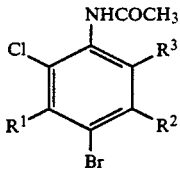

wherein $R^1$, $R^2$ and $R^3$ are as previously defined: and (d) and (e) reducing and hydrolyzing the 2-chloro or 2,6-dichloro-4-bromoanilide (IVa) of step (c) to give the 2-chloro or 2,6-dichloroaniline (1).

6. The process of claim 5 in which $R^1$ and $R^2$ are independently hydrogen or —$CH_3$.

7. The process of claim 6 in which one of $R^1$ and $R^2$ is hydrogen and the other is —$CH_3$.

8. The process of claim 7 in which $R^5$ is hydrogen.

9. A process for preparing a 2,6-dichloro-4-bromoanilide of formula (IV):

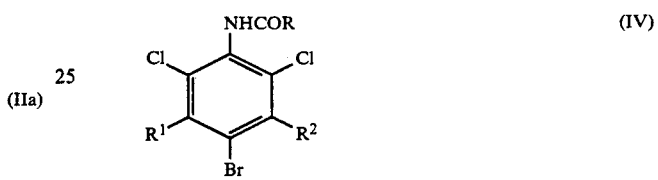

wherein

R is $CH_3$, $CH_2CH_3$ or $CF_3$, and $R^1$ and $R^2$ are independently H, $C_1$–$C_4$ alkyl, $C_1$–$C_4$ alkoxy or Cl, consisting essentially of contacting a 4-bromoanilide of formula (III):

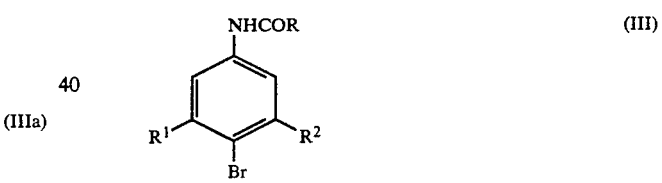

wherein

R, $R^1$ and $R^2$ are as previously defined, with from 1.8 to 2.5 equivalents of chlorine in a solvent consisting of from 3:1 to 100:1 parts of an alkanoic acid per part of water in the presence of from 0.5 to 2.0 equivalents of alkali metal bicarbonate at a temperature between about 40° C. and the freezing point of the mixture.

10. The process of claim 9 in which R is —$CH_3$.

11. The process of claim 10 in which one of $R^1$ and $R^2$ is hydrogen and the other is —$CH_3$.

* * * * *